United States Patent
Hiejima et al.

[11] Patent Number: 5,891,102
[45] Date of Patent: Apr. 6, 1999

[54] SELF-ADMINISTRATION DEVICE FOR LIQUID DRUGS

[75] Inventors: Katsuhiro Hiejima, Ohtsu; Takeshi Mori, Ibaraki, both of Japan

[73] Assignee: Nissho Corporation, Osaka-fu, Japan

[21] Appl. No.: 835,571

[22] Filed: Apr. 9, 1997

[30] Foreign Application Priority Data

Apr. 23, 1996 [JP] Japan .................................. 8-101241

[51] Int. Cl.[6] .................................................. A61M 5/178
[52] U.S. Cl. .......................................... 604/185; 604/214
[58] Field of Search .................................. 604/9, 34, 36, 604/131, 132, 133, 153, 183, 185, 212, 216, 245, 250, 256, 214; 222/95, 206, 633

[56] References Cited

U.S. PATENT DOCUMENTS

| 2,849,159 | 8/1958 | Kaufmann ................................. 604/216 |
| 3,400,716 | 9/1968 | Schultz . |
| 4,801,292 | 1/1998 | Watson .................................... 604/185 |

FOREIGN PATENT DOCUMENTS

| 5 897973A | 2/1975 | Australia . |
| 0413069A | 2/1991 | European Pat. Off. . |
| 0744182A | 11/1996 | European Pat. Off. . |
| 63-501195 | 5/1988 | Japan . |
| WO8700758 WO | 2/1987 | WIPO . |
| 9108002A | 6/1991 | WIPO . |

*Primary Examiner*—Ronald Stright
*Assistant Examiner*—A. T. Nguyen
*Attorney, Agent, or Firm*—Birch, Stewart, Kolasch & Birch, LLP

[57] ABSTRACT

A self-administration device includes a cylindrical casing opened at one end but closed at the opposite end. The closed opposite end is provided with a drug inflow port and a drug outflow port. An easily deformable and restorable reservoir is housed in the casing and is held by the closed end of the casing. The inflow port and outflow port are opened to the interior of the reservoir while a pushing device is provided at the open end of the casing and is movable along an inner wall of the casing to exert a pressure on the reservoir. A control device is provided for adjusting a moving distance of the pushing device to control a dosage of a liquid drug.

2 Claims, 6 Drawing Sheets

Fig.3
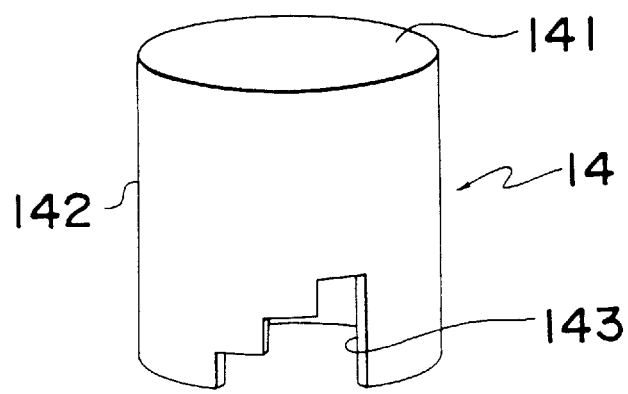
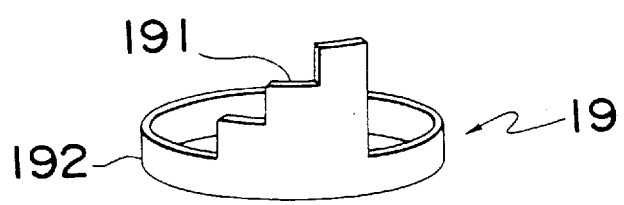
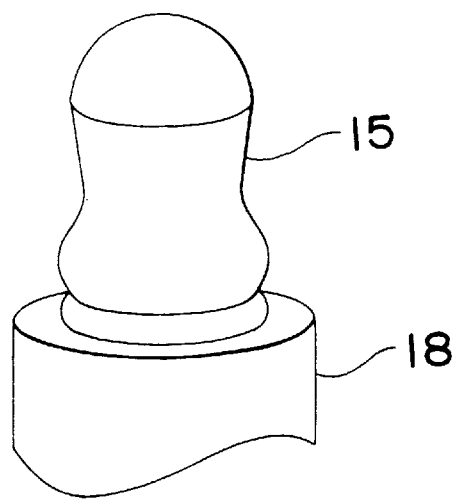

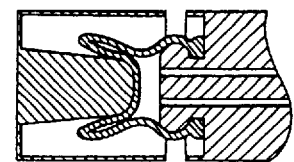
Fig. 4c
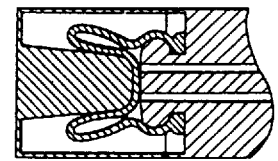
Fig. 4B
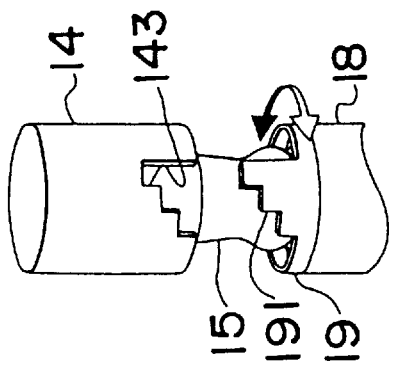
Fig. 4A
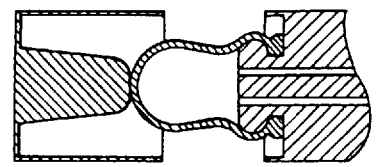

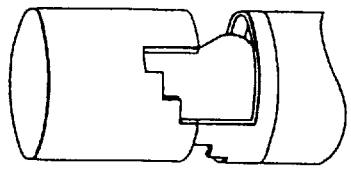
Fig. 4E
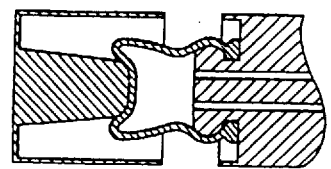
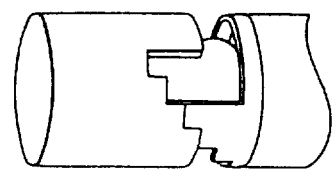
Fig. 4D
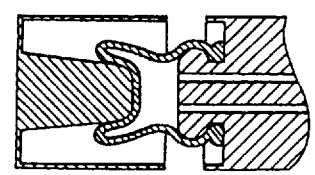

SELF-ADMINISTRATION DEVICE FOR LIQUID DRUGS

BACKGROUND OF THE INVENTION

1. Field of the Invention

The present invention relates to a self-administration device and, more particularly, to a device for administrating a liquid drug to a patient's body by himself, used solely or in combination with a system for continuous administration of a microdose of a liquid drug such as analgetic or anesthetic agent, to allay pains such as postoperative pain, cancerous pain or the like.

2. Description of the Background Art

In the recent anesthetic field, there has been used continuous epidural anesthesia or epidural catheterization with a continuous microinjector to allay the pain of a patient such as postoperative pain, cancerous pain or the like. However, patient sometimes has unique symptoms and occasionally complains of a sudden pain even in the middle of continuous administration of a microdose of analgesics. In order to cope with such a critical moment, there have been developed devices for administering a dose of an analgesic by a patient. One example of such devices is a patient-controlled analgesic delivery device disclosed in Japanese national publication 63-501195 corresponding to international publication No. WO 87/00758.

The patient's controlled analgesic delivery device of the above prior art comprises a dose reservoir 90 defined by a raised plateau 98 of a back plate 86 and a circular flexible sheet 96 as illustrated in FIG. 5. The dose reservoir 90 is connected to first and second conduits each being communicated with a medical container or a catheter. The above device further comprises a floating plate 100 rested on the flexible sheet 96, and a push button 84 arranged above the floating plate 100. The push button 84 is pivoted at its base on a pin 116 and biased by a coil spring 124 mounted around the pin 116.

If the push button 84 is pushed downward by a finger of a patient, the dose reservoir 90 is pressed by the floating plate 100 and the liquid drug in the dose reservoir 90 is delivered to the body of the patient through the conduit as illustrated in FIGS. 5B and 5C. If the finger is released from the push button 84, the button 84 is returned to its original state by the coil spring 124 as illustrated in FIG. 5D.

In the above device, however, the flexible sheet 96 is scarcely restored to its original state by itself because of its poor restoring force even when the push button 84 is released from the pushing force and returned to its original state as shown in FIG. 5D. Thus, the dose reservoir 90 can be restored to its original state only when the flexible sheet 96 is filled out by a fresh liquid drug introduced into the dose reservoir 90 from a medical container. However, the medical container is so designed as to send out a microdosage of the liquid drug by a restoring force of a balloon. Thus, it takes a long time to fill up the dose reservoir 90 because of a low pumping rate of the medical container for microdose administration. For this reason, it is difficult with the self-administration device of the prior art to administer an additional dose of the liquid drug in short order because of a long refilling time.

Further, the self-administration device of the prior art is limited in dosage by the predetermined fixed volume of the dose reservoir, thus making it impossible to administer any desired dosage of the liquid drug in the critical moment. Another problem is that, as can be seen from FIG. 5, the self-administration device of the prior art is very complex in structure and high in production cost. Further, there is a fear of leakage of the liquid drug from the circumference of the flexible sheet 96.

SUMMARY OF THE INVENTION

It is therefore an object of the present invention to provide a self-administration device which is short in recharging time, optionally selectable in dosage, free from any trouble such as leakage of liquids, and low in production cost.

The above and other objects of the present invention are achieved by providing a self-administration device comprising: a cylindrical casing opened at one end but closed at the opposite end, said closed opposite end being provided with a drug inflow port and a drug outflow port; an easily deformable and restorable reservoir housed in said casing and held by the closed end of said casing; pushing means provided at the open end of said casing and being movable along an inner wall of said casing to exert a pressure on said reservoir; and control means for adjusting a moving distance of said pushing means to control a dosage of a liquid drug, said inflow port and outflow port of said casing being opened to the interior of said reservoir.

The pushing means consists of a bottom-closed cylindrical member having a projection provided on its inner bottom wall and extended toward its open end. The dosage control means comprises an annular member having a step-formed engaging portion provided adjacent to the closed end of the casing and a notched portion formed in the side wall of the pushing means so that it engages with the engaging portion of the annular member. Preferably, the casing is provided with a slit giving access to the annular member to turn it around its axis.

In use, when the pushing means is pushed by a patient, the pushing means moves along the inner wall of the casing, and the reservoir is compressed by the projection provided on the inner wall of the casing, so that the liquid drug in the reservoir is pushed out therefrom and injected through the outflow port. Then, the reservoir is restored to its original state by its restoring force as soon as the finger is removed from the pushing means so that the interior of the reservoir becomes a negative pressure and sucks another dose of a fresh liquid drug through the inflow port within a very short time. Accordingly, the injection device of the present invention makes it possible to administer a second or another dose of a liquid drug at once, which in turn makes it possible to administer any desired amount of the liquid drug by repeating the administration of the liquid drug. Although a dosage of the liquid drug is determined by the stroke or a moving length of the pushing means, this dosage of liquid drug may be adjusted by selecting an engaging position of the annular member to the notched portion of the pushing means.

The present invention will become apparent from the detailed description given hereinafter with reference to the accompanying drawings. However, it should be understood that the detailed description and specific examples, while indicating preferred embodiment of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 3 is an exploded perspective view illustrating a relationship between a dosage control means and a reservoir used in the self-administration device of FIG. 1;

FIGS. 4A, 4B, 4C, 4D, and 4E are each a schematic diagram illustrating changes of the pushed state of reservoir depressed by the pushing means when changing the engaging position of the annular member to the notched portion;

Referring now to FIG. 1, there is shown a self-administration device according to the present invention, which comprises a cylindrical casing 11 provided at its closed end with a drug inflow port 12 and a drug outflow port 13, a reservoir 15 housed in the casing 11, a pushing means 14 provided at an open end of the casing 11, and a dosage control means for adjusting a moving length of the pushing means 14 to several steps. The inflow port 12 and outflow port 13 of the casing 11 are opened to an interior of the reservoir 15. This device is so designed that, when the pushing means 14 is pressed by the patient, the pushing means 14 is moved by a distance determined by the dosage control means and the reservoir 15 is depressed and deformed by the pushing means 14, thereby delivering the liquid drug in the reservoir 15 to the outside of the reservoir 15. The dosage of the liquid drug is determined by the moving distance of the pushing means 14.

Figure 1:
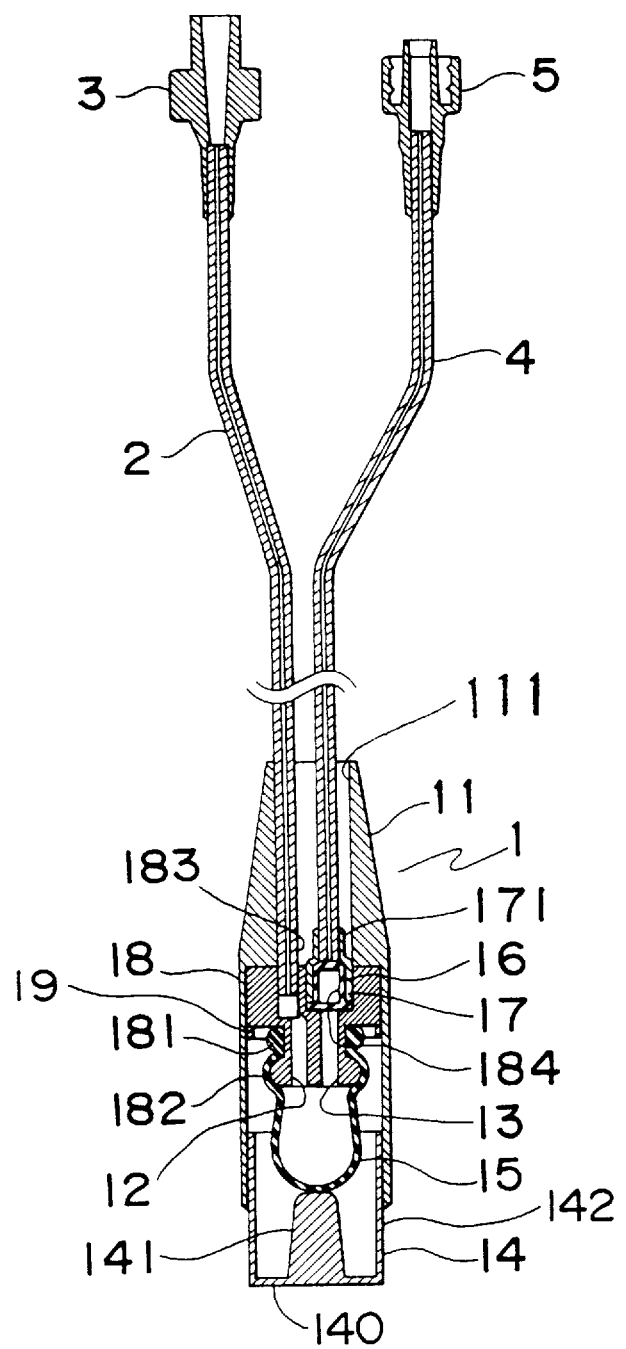
FIG. 1 is a cross sectional view showing an embodiment of a self-administration device of the present invention.

The casing 11 is a cylindrical member opened at one end but closed at the other end and generally made of a transparent synthetic resin such as polyethylene, polypropylene, polyester or the like. The close end of the casing 11 is provided with the drug inflow port 12 and the drug outflow port 13. Although the closed end of the casing 11 may be formed as an integral part of the casing 11, it is preferred to form it as a separate member as shown in FIG. 1 so that the reservoir 15 and a stop valve 16 can be assembled in the casing with ease.

In the embodiment of FIG. 1, the casing 11 is composed of a cylindrical member with a stepped lumen, i.e., a large-sized lumen and a small-sized lumen, and a closing member 18 fitted in the large-sized lumen of the casing 11 and seated on the stepped wall of the large-sized lumen. The small-sized lumen of the casing 11 is used as an insertion hole 111 for attachment of tubes 2 and 4. The closing member 18 is shaped in the form of a disk and provided at its one flat end with a projection or port-forming portion 181 having the drug inflow port 12 and the drug outflow port 13. The closing member 18 is so arranged in the large-sized lumen of the casing 11 that the port-forming portion 181 is directed to the open end of the casing 11. The opposite side of the closing member 18 facing to the insertion hole 111 is provided with a hole 183 for communication of the drug inflow port 12, to an upstream drug tube 2, and a hole 184 for communication of the drug outflow port 13 to a downstream drug tube 4. As illustrated in FIG. 1, there may be provided a check valve 16 in the hole 184 to prevent the liquid from flowing in the reverse direction.

The port-forming portion 181 of the closing member 18 is provided with an annular rib 182 at its distal end to prevent the reservoir 15 from slipping out of place. The closed end of the casing 11 may be provided with projections (not illustrated in the drawings) for attachment of the upstream drug tube 2 and downstream drug tube 4, instead of provision of tube insertion hole 111.

The check valve 16 is provided for prevention of back flow of the liquid drug from the downstream drug tube 4 toward the reservoir 15. The check valve 16 is generally located, as illustrated in FIG. 1, in the hole 184 of the closing member 18 and fixed thereto by a holding member 17 having a connecting end 171 to which the downstream tube 4 is connected. The preferred check valve is of a duck bill type or of a ball valve type, though the check valve is not limited thereto. The check valve 16 is not necessarily provided in the device body 1 and may be arranged in the downstream drug tube 4 or in a Lure connector 5.

The reservoir 15 is attached to the port-forming portion 181 of the closing member 18 and thus the drug inflow port 12 and drug outflow port 13 are opened to the reservoir 15. The reservoir 15 is prevented by the annular rib 182 from slipping out of place. The reservoir 15 is a container for reserving a liquid drug fed from the medical container 6 and is easily deformable by pressure and has the ability to restore to its original shape. The reservoir 15 is generally made of an elastic material such as flexible resin, natural rubbers, or synthetic rubbers to give it flexibility and restoring force. The preferred flexible resin include polyethylene, polypropylene, polyester and the like, while the synthetic rubbers includes silicone rubber, olefin elastomers and the like.

The pushing means 14 is generally made of synthetic resin such as polyethylene, polypropylene or polyester in the form of a bottom-closed cylindrical member composed of a bottom 140 and a cylindrical side wall 142. As shown in FIG. 1, the pushing means 14 is provided on its inner bottom wall 140 with a projection 141 to make it easy to push or depress the reservoir 15. The pushing means 14 is fitted in the large-sized lumen of the casing 11 similar to a nest. The pushing means 14 is movable along the inner wall of the casing 11 to depress the reservoir 15 at the inner wall of the bottom 140.

Adjacent to the closing member 18 there is provided an annular member 19. As best shown in FIG. 3, the annular member 19 is composed of an annular base portion 192 and a stepped engaging portion 191 and arranged coaxially and rotatably on the closing member 18 so that the stepped engaging portion 191 is directed toward the reservoir 15. This annular member 19 constitutes dosage control means in cooperation with a stepped notch 143 provided in the side wall of the pushing means 14. The stepped notch 143 of the pushing means 14 is formed into a configuration complementary to the stepped engaging portion 191 of the annular member 19 and engages therewith in various forms, for example, in four forms as illustrated in FIG. 4. In FIG. 4B, the stepped notch 143 of the pushing means 14 is engaged at its all steps with the steps of the stepped engaging portion 191, while in FIG. 4E the stepped notch 143 of the pushing means 14 is engaged with the step of the stepped engaging portion 191 at its only one step or end.

The engagement between the stepped engaging portion 191 and the stepped notch 143 is selected by turning the annular member 19 coaxial with the casing 11 on its axis. In order to make it possible to turn the annular member 19 on its axis, the embodiment of FIG. 1, the side wall of the casing 11 is provided with a circumferential slit 112 at the position corresponding to that of the annular base portion 192 of the annular member 19 so that a pin or a suitable tool (not illustrated in the drawings) can be inserted from the outside into the slit 112. The annular member 19 may be turned on its axis coaxial with the casing 11 by any suitable operating means, for example, by operating a knob or a projection (not illustrated in the drawings) provided on the annular member 19 and extending outward through the slit 112 so as to be operated by the finger.

Figure 2:
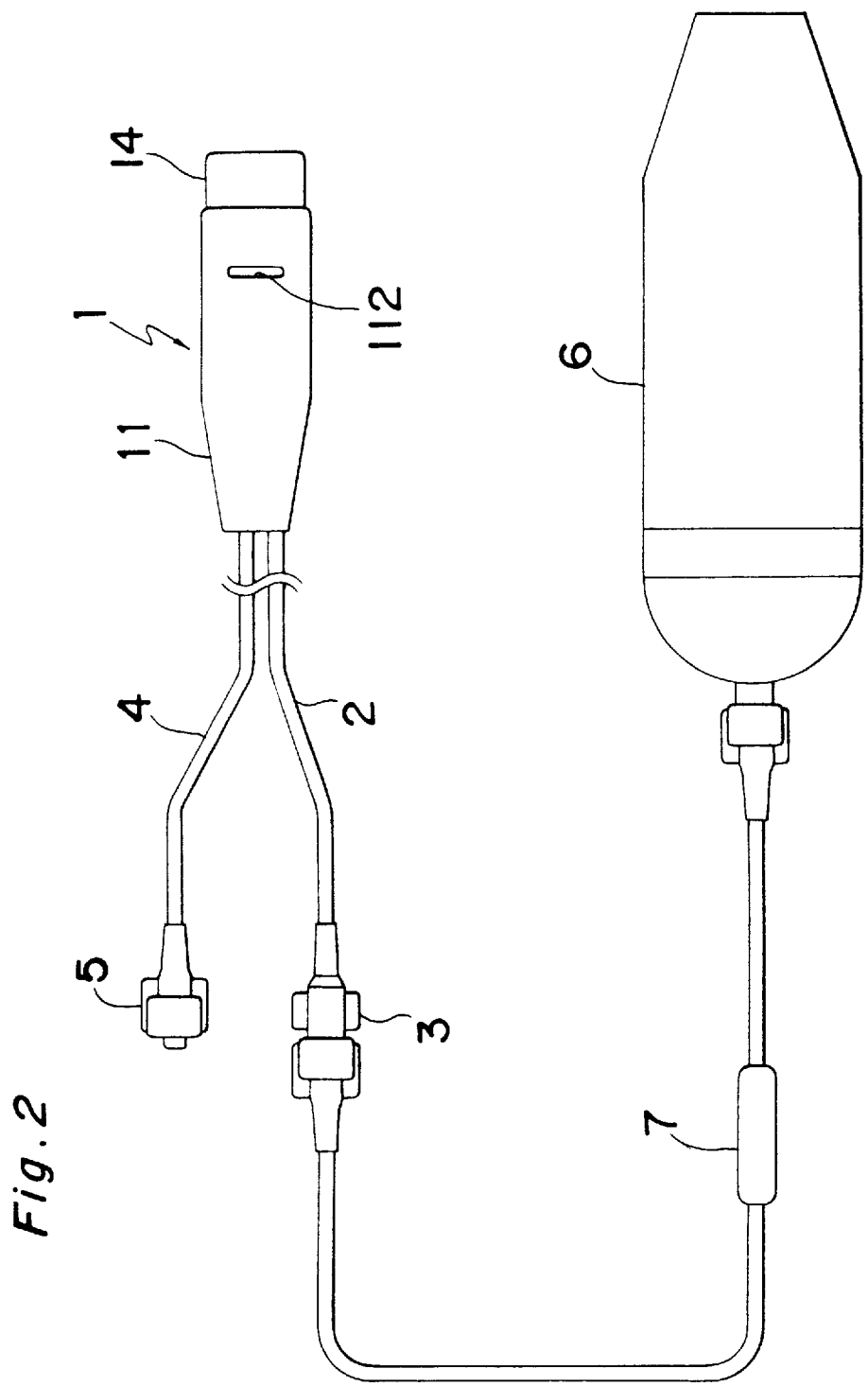
FIG. 2 is a plan view of the self-administration device of FIG. 1 with a medical container connected thereto through a flow control means.
Figure 5A:
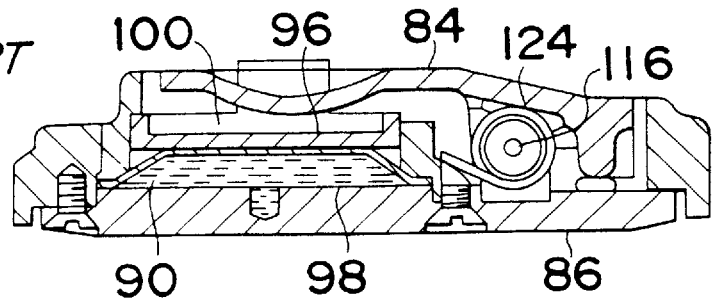
FIGS. 5A, 5B, 5C, and 5D are each cross sectional views of an apparatus of the prior art, illustrating operation of the apparatus.
Figure 5B:
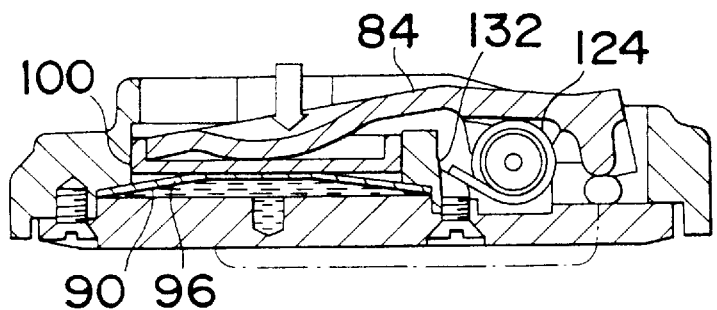
Figure 5C:
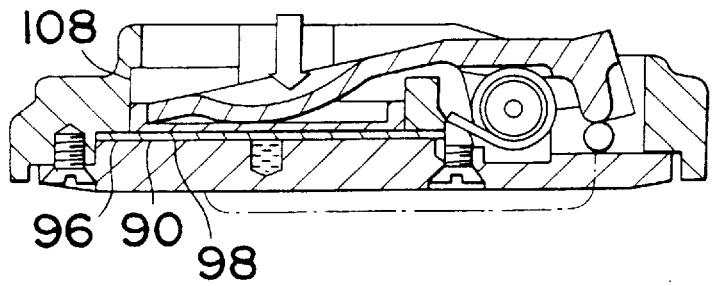
Figure 5D:
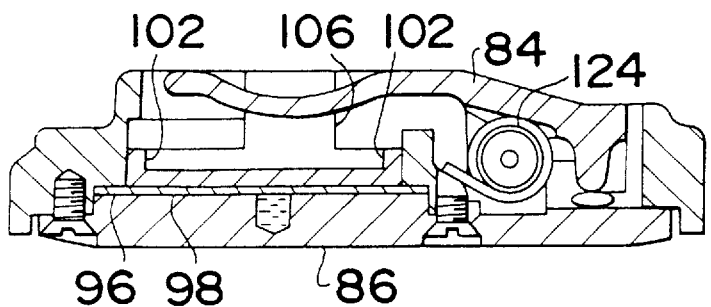

The self-administration device is completed by connecting the upstream drug tube 2 and downstream drug tube 4 to the device body 1. These tubes 2 and 4 have a suitable connecting means such as, for example, a Lure connector 3, 5 illustrated in FIG. 1, for connection to other devices. The self-administration device may have a liquid drug container 6 connected thereto directly or through a flow control means 7, as illustrated in FIG. 2. As the liquid drug container 6 to be connected to the self-administration device of the present invention, are those including a balloon, such as disclosed in Japanese examined publication Nos. 6-77604 6-83725 (which corresponds to U.S. Pat. No. 5178610. The self-administration device of the present invention may be used by directly connecting it the dropper of an infusion set.

As mentioned above, the self-administration device of the present invention is easy to operate, takes a short time for recharging the reservoir with the liquid drug, and makes it possible to control the dose of the liquid drug, and free from troubles such as leakage. Thus, it is suitable for administration of a liquid drug to a patient by one shot. Further, it is inexpensive, thus making it possible to reduce a charge to the patient.

The invention being thus described, it will be obvious that the same may be varied in many ways. Such variations are the invention, and all such modifications as would be obvious to one skilled in the art were intended to be included within the scope of the following claims.

What is claimed is:

1. A self-administration device comprising:
    a cylindrical casing opened at one end but closed at the opposite end, said closed opposite end being provided with a drug inflow port and a drug outflow port;
    an easily deformable and restorable reservoir housed in said casing and held by the closed end of said casing;
    manual pushing means provided at the open end of said casing and being movable along an inner wall of said casing to exert a pressure on said reservoir; and
    control means for adjusting a moving distance of said manual pushing means to control a dosage of liquid drug, said control means disposed around said inflow and said outflow port and engaging with said manual pushing means, said inflow port and outflow port of said casing being opened to the interior of said reservoir, whereby the dosage of the liquid drug is adjusted according to a position of said control means relative to said manual pushing means.

2. The self-administration device according to claim 1, wherein said pushing means includes a bottom-closed cylindrical member having a projection provided on its inner bottom wall, the dosage control means comprises an annular member having a step-formed engaging portion provided adjacent to the closed end of the casing and a notched portion formed in the side wall of the pushing means so that it engages with the engaging portion of the annular member, and the casing is provided with a slit giving access to the annular member to turn it around its axis.

* * * * *